US012778854B2

(12) United States Patent
Bayoumi

(10) Patent No.: US 12,778,854 B2
(45) Date of Patent: Nov. 3, 2026

(54) GUIDED COLORED NASOGASTRIC TUBE (GCNGT)

(71) Applicant: UNIVERSITY OF BAHRAIN, Sakhir (BH)

(72) Inventor: Magda Mohamed Mohamed Bayoumi, Muharraq (BH)

(73) Assignee: University of Bahrain, Sakhir (BH)

( * ) Notice: Subject to any disclaimer, the term of this patent is extended or adjusted under 35 U.S.C. 154(b) by 364 days.

(21) Appl. No.: 18/702,113

(22) PCT Filed: Mar. 4, 2024

(86) PCT No.: PCT/IB2024/052074
§ 371 (c)(1),
(2) Date: Apr. 17, 2024

(87) PCT Pub. No.: WO2025/186594
PCT Pub. Date: Sep. 12, 2025

(65) Prior Publication Data

US 2026/0157936 A1 Jun. 11, 2026

(51) Int. Cl.
*A61J 15/00* (2006.01)
*A61B 5/145* (2006.01)
*A61M 25/09* (2006.01)

(52) U.S. Cl.
CPC ....... *A61J 15/0084* (2015.05); *A61J 15/0007* (2013.01); *A61B 5/14539* (2013.01); *A61J 2205/20* (2013.01); *A61M 2025/09133* (2013.01); *A61M 2025/09175* (2013.01)

(58) Field of Classification Search
CPC ................ A61J 15/0084; A61J 15/0007; A61J 2205/20; A61B 5/14539; A61M 2025/09133; A61M 2025/09175
See application file for complete search history.

(56) References Cited

U.S. PATENT DOCUMENTS

| | | | | |
|---|---|---|---|---|
| 4,771,782 A * | 9/1988 | Millar | A61B 5/14539 600/561 |
| 4,850,358 A * | 7/1989 | Millar | A61M 25/01 600/561 |
| 5,105,812 A | 4/1992 | Corman | |
| 5,391,158 A | 2/1995 | Peters | |
| 6,701,918 B2 | 3/2004 | Fariss et al. | |

(Continued)

FOREIGN PATENT DOCUMENTS

| | | |
|---|---|---|
| CA | 2712361 | 7/2017 |
| CN | 209662232 | 11/2019 |

(Continued)

OTHER PUBLICATIONS

International Search Report and Written Opinion issued in corresponding PCT Application No. PCT/IB2024/052074, mailed May 9, 2024, 7 pages.

*Primary Examiner* — Cris L. Rodriguez
(74) *Attorney, Agent, or Firm* — Norton Rose Fulbright US LLP

(57) ABSTRACT

Disclosed are guide wires for use in a nasogastric tube, nasogastric tube assemblies with such guide wires, and methods of placing such nasogastric tube assemblies in a stomach. The guide wire comprises a wire body, a clip attached to the wire body, and a color changing pH indicator. The guide wire may include a wire body and a coating material.

20 Claims, 7 Drawing Sheets

(56) References Cited

U.S. PATENT DOCUMENTS

| | | | | |
|---|---|---|---|---|
| 10,687,731 | B2 | 6/2020 | Bennet-Guerrero | |
| 2008/0004598 | A1 | 1/2008 | Gilbert | |
| 2013/0172781 | A1 | 7/2013 | Russo | |
| 2018/0078195 | A1 | 3/2018 | Sutaria et al. | |
| 2019/0240115 | A1 | 8/2019 | Elia | |
| 2021/0268241 | A1* | 9/2021 | Lydecker | A61B 17/12099 |
| 2023/0200845 | A1* | 6/2023 | Klein | A61M 25/09 606/185 |
| 2024/0416026 | A1* | 12/2024 | Smith | A61M 1/916 |

FOREIGN PATENT DOCUMENTS

| | | |
|---|---|---|
| CN | 212166168 | 12/2020 |
| CN | 213466061 | 6/2021 |
| CN | 215024768 | 12/2021 |
| CN | 215230446 | 12/2021 |
| CN | 217660775 | 10/2022 |
| CN | 219423534 | 7/2023 |
| EP | 2416833 | 6/2015 |
| JP | 2018524042 | 8/2018 |
| TW | M626685 | 5/2022 |

* cited by examiner

GUIDED COLORED NASOGASTRIC TUBE (GCNGT)

CROSS-REFERENCE TO RELATED APPLICATION

This application is a national phase application under 35 U.S.C. § 371 of International Application No. PCT/IB2024/052074, filed Mar. 4, 2024, the contents of which is incorporated into the present application by reference in its entirety.

FIELD

The invention relates generally to medical devices and intubation and, more particularly, but not by way of limitation, to tubes for use during intubation procedures (e.g., nasogastric intubation and/or orogastric intubation), and methods utilizing such tubes.

BACKGROUND

A nasogastric tube may be placed into a patient through the patient's nose, passing the throat and esophagus, and into the stomach. Nasogastric tubes are useful to deliver nutrients and medications to patients in need. However, insertion of nasogastric tube, also known as nasogastric intubation, is a procedure that needs trained healthcare providers with special skills to avoid potentially serious complications to the patients.

One exemplary technical challenge of nasogastric intubation is to determine whether the nasogastric tube is correctly placed into a stomach. Existing techniques to confirm placement of a nasogastric tube include: 1) conducting X-ray imaging to determine the placement of the nasogastric tube; 2) applying Whoosh's test by auscultating the air insufflated through the nasogastric tube into the stomach; 3) considering the absence of respiratory distress as an indicator of correct placement; 4) using pH indicator papers to measure pH value of the nasogastric aspirate; 5) using an endoscope to determine the placement of the nasogastric tube; and 6) using smart devices to track the placement of the nasogastric tube.

However, those existing techniques can be costly, inaccurate, inconvenient, and/or not suitable for healthcare facilities with limited resources. For example, X-ray imaging is expensive and may not be available in primary health facilities, private clinics, or home care centers. Moreover, it is difficult to perform X-ray imaging every time before feeding a patient to confirm the placement of the nasogastric tube, especially for patients who are already connected with sophisticated technical life support devices. As another example, using an endoscope requires mild to moderate sedation and physician supervision. Thus, an endoscopic procedure can be costly and not easily available or accessible. Furthermore, sedation required by using an endoscope may conflict with the nasogastric intubation procedure because nasogastric intubation requires the patient to be oriented and alert to help in the insertion of the tube in the correct place by swallowing to ensure correct placement. As yet another example, using smart devices requires trained medical staff and regular device maintenance, which can be costly and limit accessibility.

SUMMARY

A discovery has been made that provides a solution, disclosed herein, to at least one or more of the aforementioned problems. Disclosed includes embodiments of apparatuses, systems, and methods. In one aspect, disclosed is a guide wire for use in a nasogastric tube. The guide wire may include a wire body, a clip, and a color changing pH indicator. The wire body may include a distal end and a proximal end. The clip may be attached to the wire body at or within 15 centimeters of the distal end of the wire body. The clip may include a top cover and a bottom cover. The bottom cover may be movably connected to the top cover. The clip may be capable of being in an open position or a closed position. In the closed position, the clip may be capable of holding the color changing pH indicator. In the open position, the clip may be capable of releasing the color changing pH indicator.

As an exemplary use case, the guide wire together with the nasogastric tube may be inserted into a patient. If the nasogastric tube is correctly placed in a stomach, the color changing pH indicator will display a color change upon contacting with gastric juice, which is acidic and may have a pH level from 1.5 to 2.0. The color changing pH indicator may be retrieved by removing the guide wire from the nasogastric tube. The pH indicator may be viewed or the displayed color change may be read to determine if the placement of the nasogastric tube is correct. Thus, as an exemplary benefit, this solution can provide a safer, faster, and more accurate method to examine the placement of a nasogastric tube. Moreover, the color changing pH indicator may be easily replaceable. In some instances, the placement of a nasogastric tube may be examined multiple times as needed while the nasogastric tube remains inserted in the patient. For example, the pH indicator may be replaced with a replacement pH indicator (or another type of indicator) and re-inserted into the nasogastric tube and then removed again to view or read the replacement indicator.

In some aspects, the clip is attached to the wire body at or within 20, 19, 18, 17, 16, 15, 14, 13, 12, 11, 10, 9, 8, 7, 6, 5, 4, 3, 2, 1, or 0 centimeters of the distal end of the wire body. In some instances, the distal end of the wire body extends into an inner chamber of the clip. In some instances, the clip is attached to the wire body in a removable manner, such as by a removable bolt, a snap fitting, or a threaded connection. In some instances, the clip is attached in a permanent manner, such as a weld or a rivet.

In some aspects, the guide wire further includes an enlarged head at the proximal end of the wire body. The enlarged head may be made of a metal and/or a plastic. The enlarged head may have a size at the largest dimension of 2 to 15 centimeters, such as 2, 3, 4, 5, 6, 7, 8, 9, 10, 11, 12, 13, 14, or 15 centimeters. In some instances, the enlarged head is in the shape of a handle.

In some aspects, material of the wire body includes a base material and a coating material. The coating material may be a polymer and/or a lubricant. In some instances, the coating material is a polyurethane. In some instances, the base material is a flexible metal and/or plastic. In some aspects, the base material includes flexible steel.

In some aspects, material of the clip includes a polymer, rubber, and/or metal. In some instances, the material of the clip includes latex, a silicone, a polyvinyl chloride, and/or a polyurethane. In some instances, the material for the clip includes aluminum and/or stainless steel. In some instances, the material for the clip includes polyurethane, silicone, or a combination thereof.

In some aspects, the top cover of the clip forms a convex surface and two oblong side walls, together defining an inner chamber. In some aspects, the convex surface is half-oval shaped.

In some aspects, the top cover and the bottom cover are movably connected. The movable connection may be a hinge. In some aspects, the top cover or bottom cover forms two side slots at a proximal end of the top cover or bottom cover. In some aspects, the bottom cover or the top cover forms a ring holder at a proximal end of the bottom cover or top cover. In some instances, the top cover and bottom cover are connected by a hinge that may include an axial pin. The axial pin may contact the ring holder and the two side slots to form a movable connection between the top cover and the bottom cover. In some instances, the hinge is spring loaded, or requires force to move the clip into the open position even after any latch capable of locking the clip in the closed position has been released.

In some aspects, the bottom cover and/or top cover includes a plurality of protrusions that project towards the inner chamber defined by the top cover when the clip is in the closed position. In some aspects, the plurality of protrusions are arranged in one or more rows, such as two rows of three protrusions. In some aspects, the plurality of protrusions are not arranged in a row. In some aspects, the protrusions are cylindrical. In some aspects, the protrusions do not extend into the inner chamber defined by the top cover. In some aspects, the protrusions extend into the inner chamber defined by the top cover when the clip is in the closed position. In some aspects, the top cover or bottom cover includes a latch capable of locking the clip in the closed position. In some aspects, the latch is capable of reversibly locking the clip in the closed position.

In some aspects, the color changing pH indicator forms one or more holes through the color changing pH indicator. In some aspects, the color changing pH indicator forms a central hole through the color changing pH indicator. In some aspects, the color changing pH indicator forms a plurality of holes that correspond to the plurality of protrusions of the top or bottom cover. In some aspects, the latch is capable of inserting through a central hole of the color changing pH indicator when the clip is in the closed position.

In another aspect, disclosed is a nasogastric tube assembly. The nasogastric tube assembly includes a nasogastric tube and any of the guide wires disclosed herein. In some aspects, the nasogastric tube includes a distal end and a proximal end and the nasogastric tube includes one or more pores at the distal end of the nasogastric tube. In some instances, the nasogastric tube includes a flexible material. In some instances, the flexible material includes a polymer or a rubber. In some aspects, the flexible material includes a latex, a silicone, a polyvinyl chloride, and/or a polyurethane.

In another aspect, disclosed is a method of placing a nasogastric tube assembly in a stomach. The method may include the steps of: 1) inserting any of the nasogastric tube assemblies disclosed herein into the esophagus, stomach, and/or lungs via a mouth or a nose; and 2) removing the guide wire from the nasogastric tube to view the color changing pH indicator. In some aspects, the method further includes replacing the color changing pH indicator with another color changing pH indicator and/or another indicator. In some instances, the method further includes reinserting the guide wire into the nasogastric tube. In some instances, the method includes sterilizing the guide wire after removing from the nasogastric tube. In some aspects, the method further includes at least partially retracting the nasogastric tube from the esophagus, stomach, and/or lungs and reinserting the nasogastric tube into the esophagus, stomach, and/or lungs. In some instances, the method comprises reinserting the guide wire into the nasogastric tube before, during, or after at least partially retracting the nasogastric tube, and reinserting the nasogastric tube into the esophagus, stomach, and/or lungs.

The term "connected" is defined as coupled, although not necessarily directly, and not necessarily mechanically; two items that are "connected" may be unitary with each other.

The terms "a" and "an" are defined as one or more unless this disclosure explicitly requires otherwise.

The term "and/or" means "and" or "or". To illustrate, A, B, and/or C includes: A alone, B alone, C alone, a combination of A and B, a combination of A and C, a combination of B and C, or a combination of A, B, and C.

The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the terms "substantially," "approximately," and "about" may be substituted with "within [a percentage] of" what is specified, where the percentage includes 0.1, 1, 5, and 10 percent.

Further, a device or system that is configured in a certain way is configured in at least that way, but it can also be configured in other ways than those specifically described.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Any embodiment of any of the apparatuses, systems, and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Details associated with the embodiments described above and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

Figure 2:
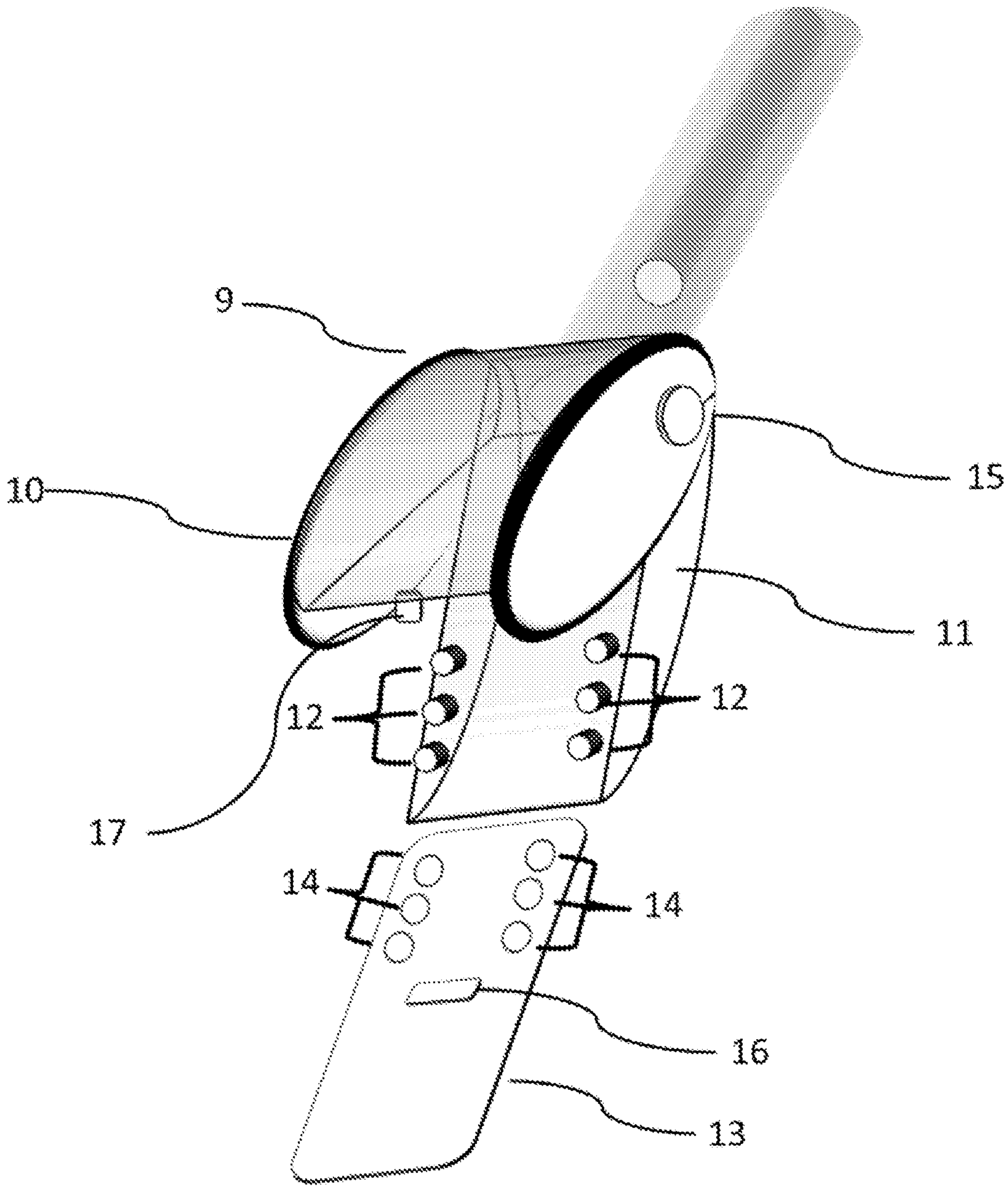

FIG. 2 depicts a perspective view of an exemplary clip in an open position with an exemplary color changing pH indicator, where the color changing pH indicator is not yet installed onto a bottom cover of the clip.

Figure 3:
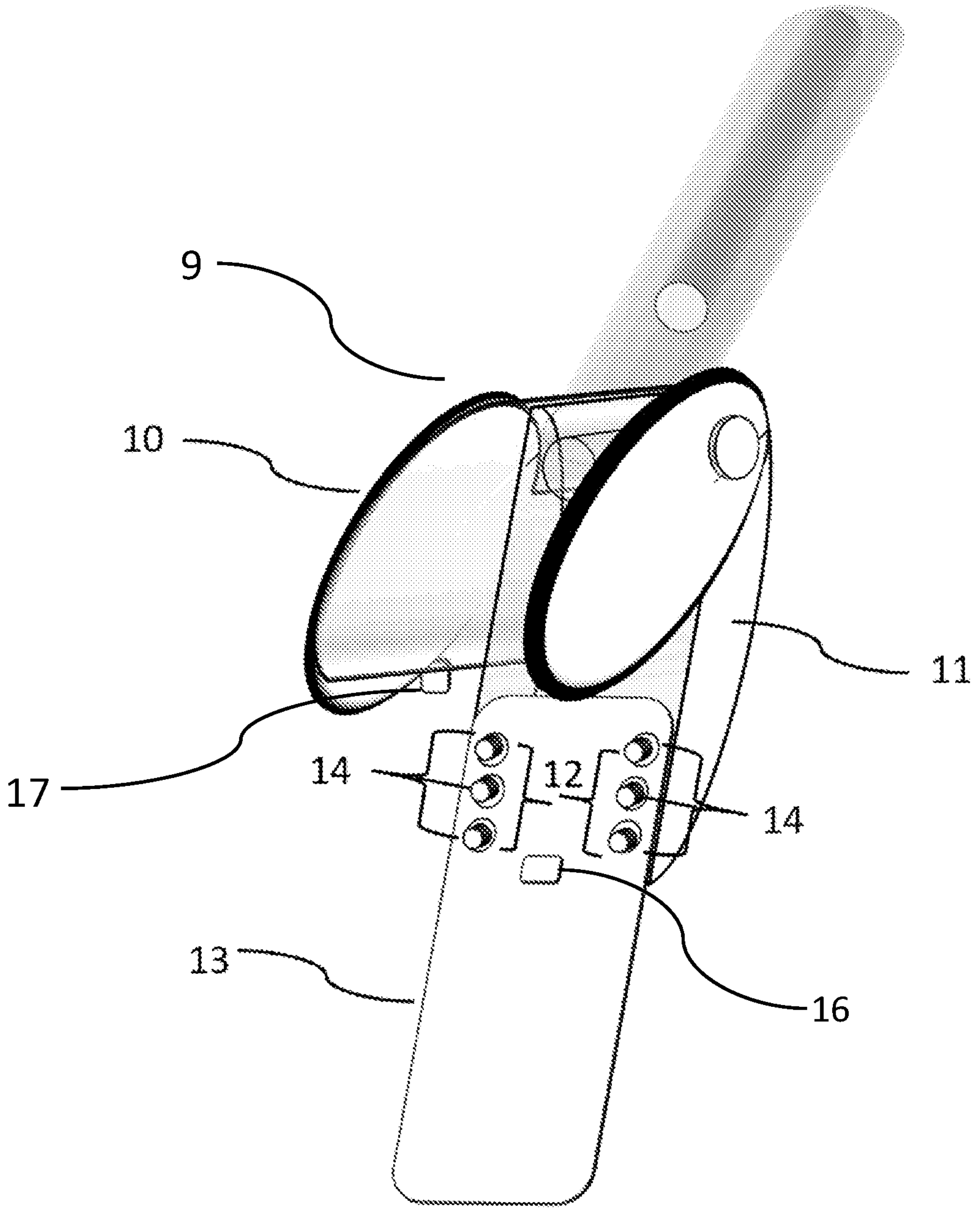

FIG. 3 depicts a perspective view of an exemplary clip in an open position with an exemplary color changing pH indicator, where the color changing pH indicator is installed onto a bottom cover of the clip.

Figure 4:
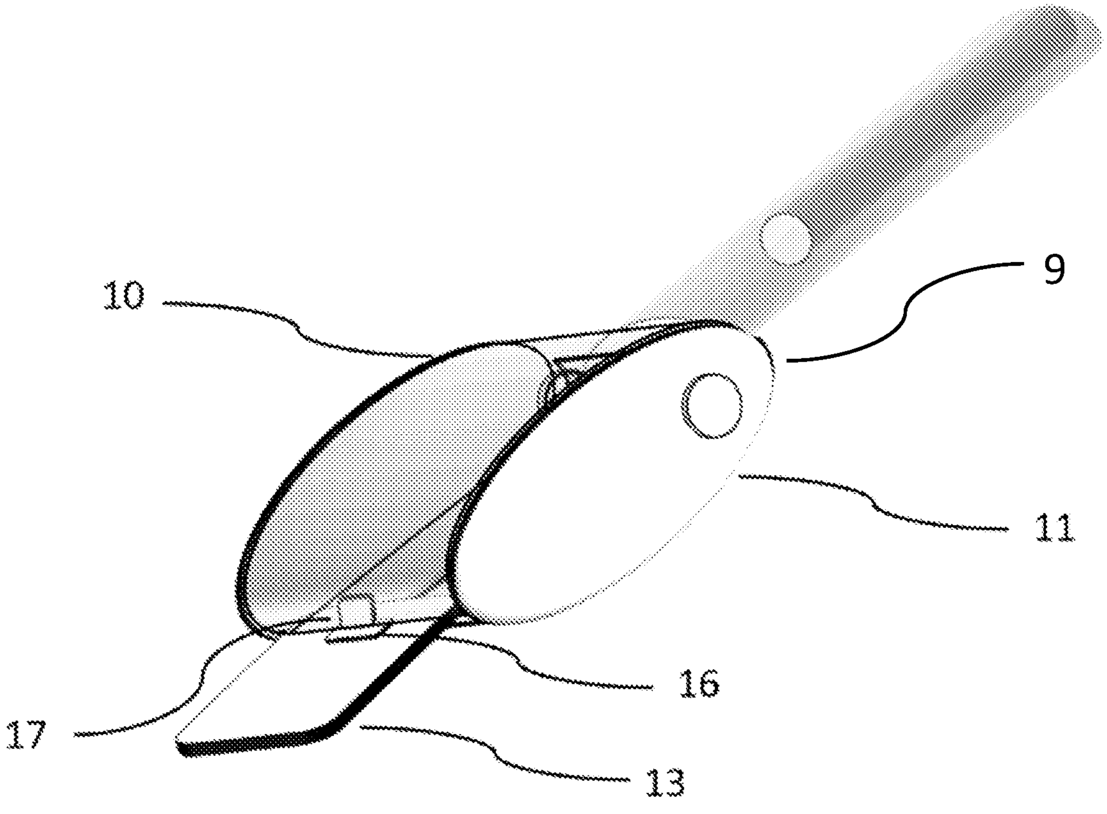

FIG. 4 depicts a perspective view of an exemplary clip in a closed position with an exemplary installed color changing pH indicator, where the clip is locked in a closed position by a latch of the top cover.

Figure 5:
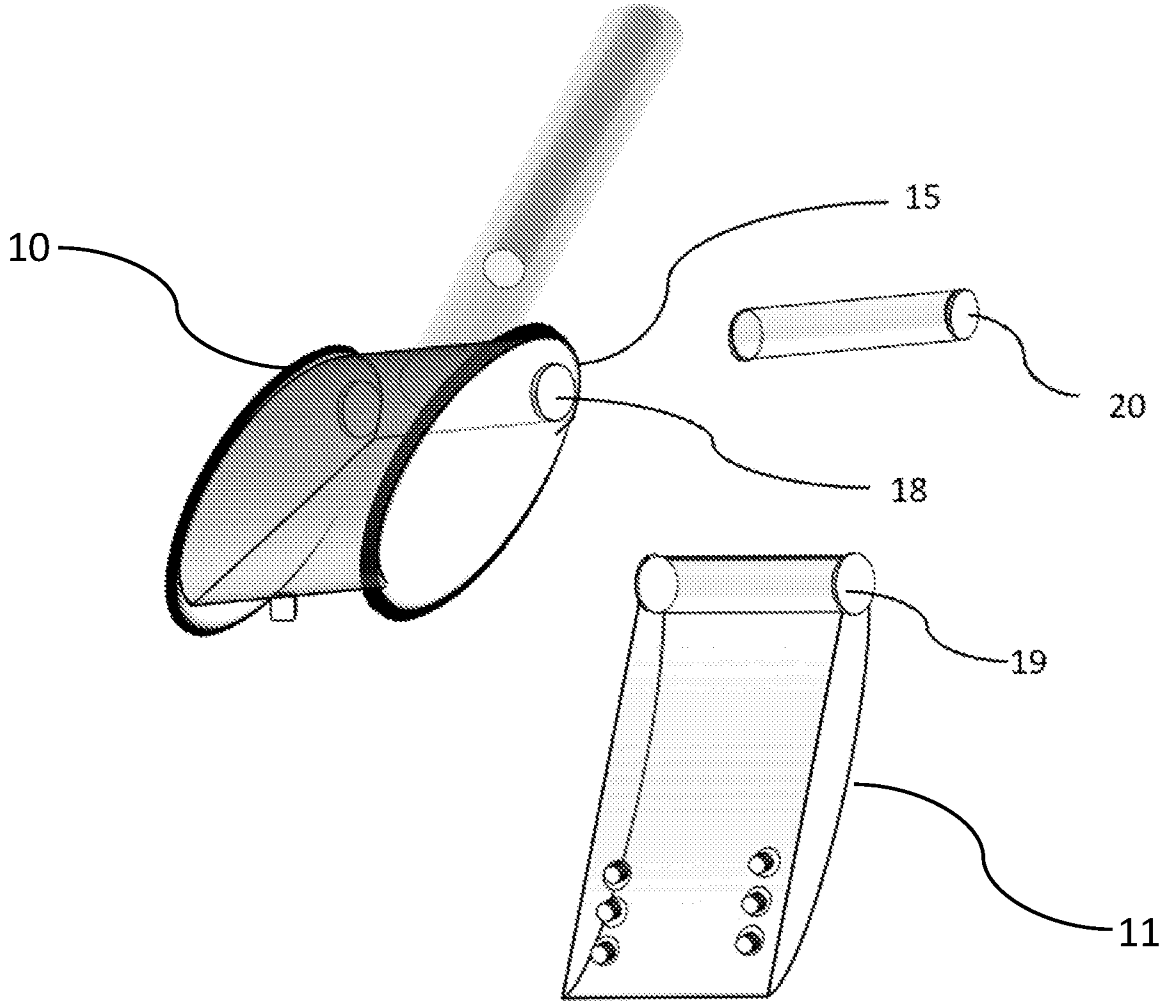

FIG. 5 depicts a perspective view of an exemplary disassembled clip, showing a top cover, an axial pin, and a bottom cover.

Figure 6:
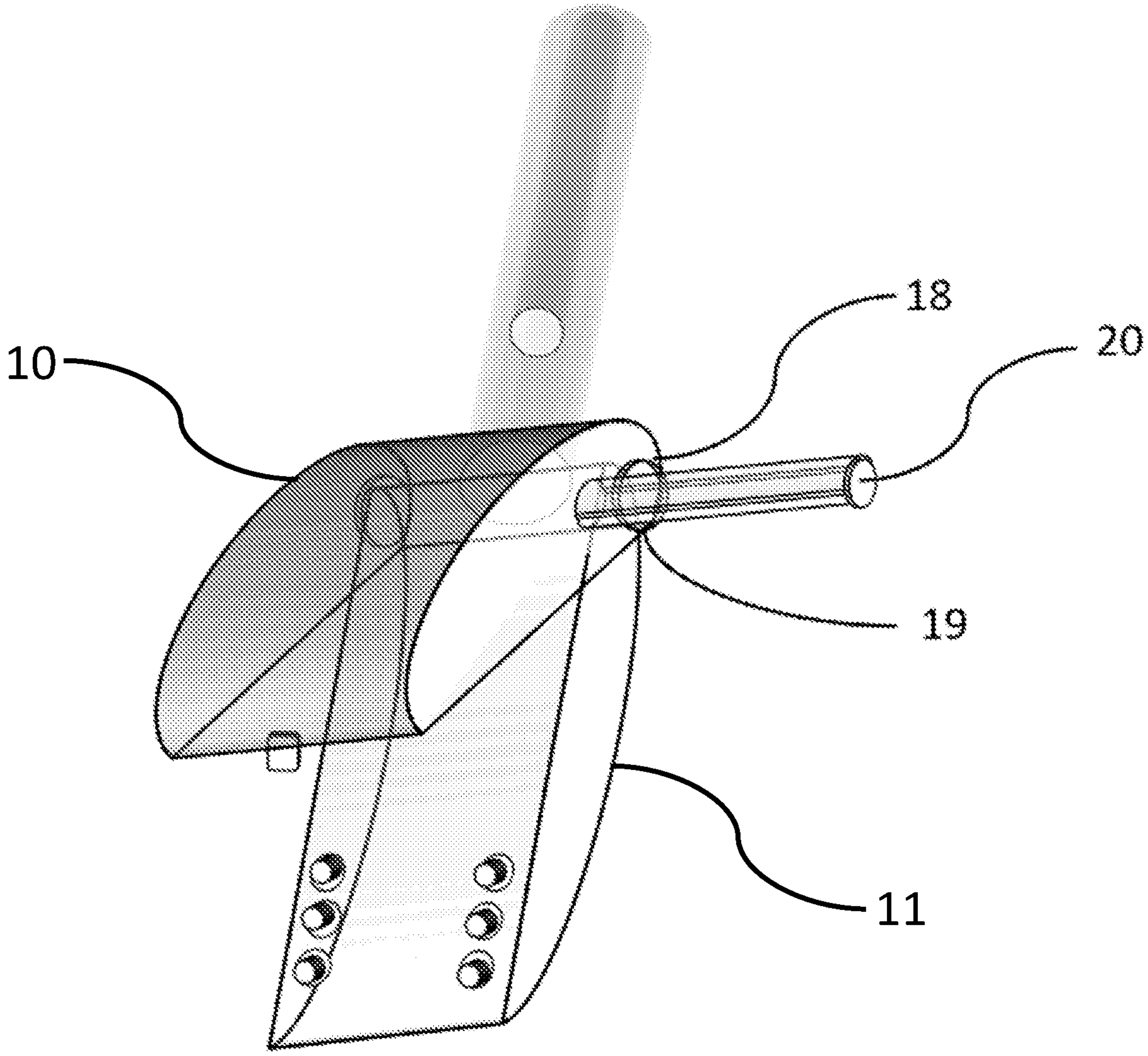

FIG. 6 depicts a perspective view of an exemplary partially assembled clip, showing a top cover, an axial pin, and a bottom cover.

Figure 7:
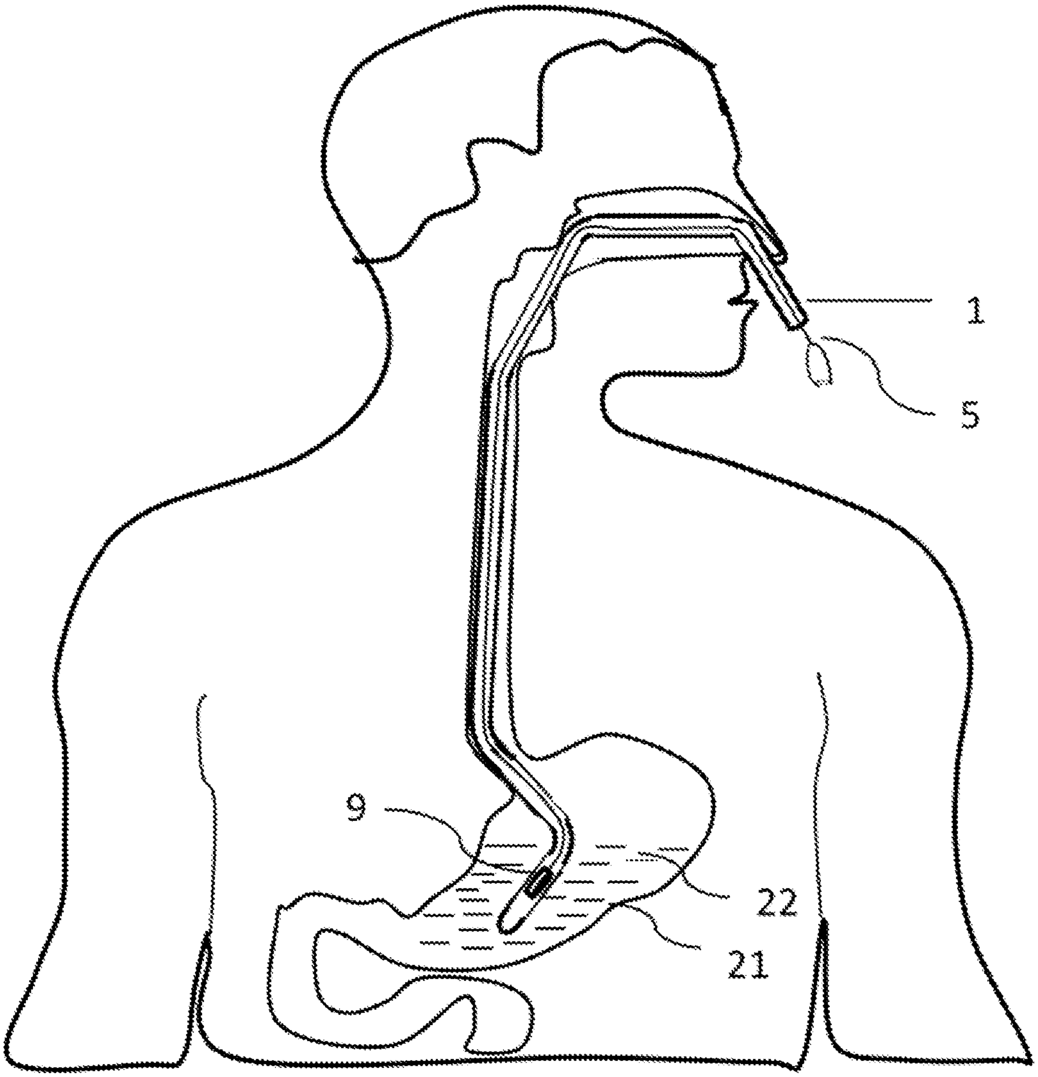

FIG. 7 depicts a cross-sectional view of insertion of an exemplary nasogastric tube and an exemplary guide wire, including a wire body, a clip, and an exemplary color changing pH indicator, into a stomach of a patient.

DESCRIPTION OF ILLUSTRATIVE EMBODIMENTS

Figure 1:
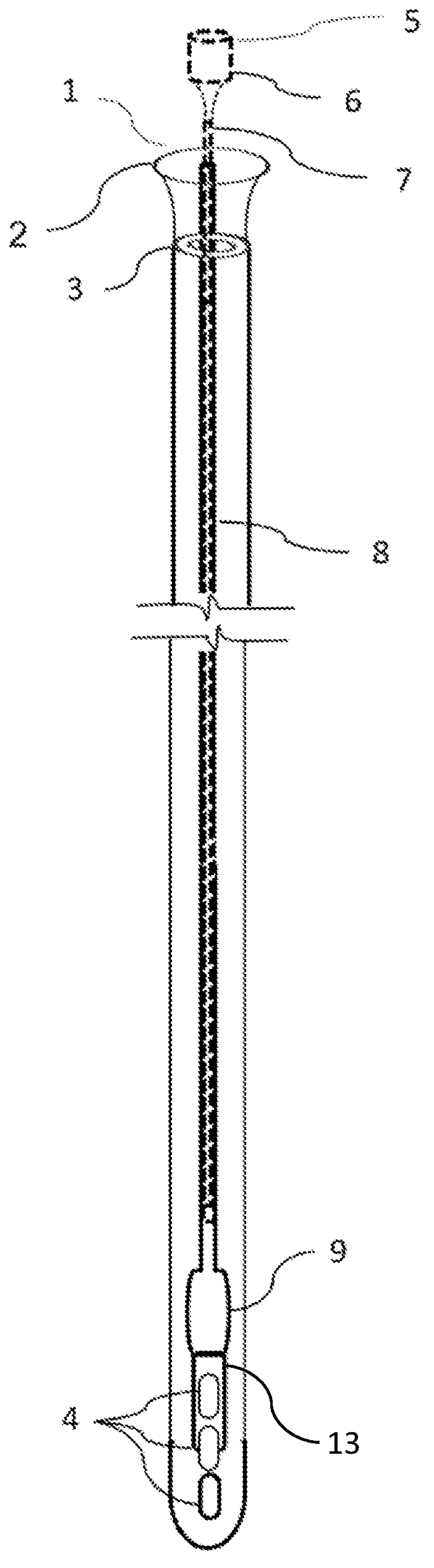
FIG. 1 depicts an overview of an exemplary nasogastric tube including a distal end and a proximal and depicting an exemplary guide wire therein. The exemplary guide wire includes: a wire body including a distal end and a proximal end; a clip attached to the wire body at or within 15 centimeters of the distal end of the wire body; and an exemplary color changing pH indicator. The nasogastric tube forming openings at the distal end.

Referring now to the drawings, and more particularly to FIG. 1, showing an overview of an exemplary nasogastric tube 1 with a guide wire 5. Guide wire 5 includes: a wire body 7 including a distal end and a proximal end; a clip 9 attached to the wire body 7 at or within 15 centimeters of the distal end of the wire body 7; and a color changing pH indicator. Nasogastric tube 1 includes nasogastric tube head 2 and nasogastric tube body 3. Nasogastric tube 1 has a distal end and a proximal end, and Nasogastric tube 1 forms one or more pores 4 at the distal end. Nasogastric tube 1 encloses a guide wire 5 that includes a wire body 7, a clip 9, and a color changing pH indicator 13. Wire body 7 includes a distal end and a proximal end and may include an enlarged head 6 at the proximal end. Enlarged head 6 provides an enlarged contact surface for a person to hold, insert, retract, or otherwise operate guide wire 5. Material of wire body 7 includes a base material (not separately shown) and a coating material 8. Material of guide wire 5, including the base material of wire body 7 and/or the coating material 8, may include a metallic material, a plastic material, a silicone material, or any combination of metallic, silicone, and/or plastic materials. As an example, the base material may include flexible steel. As another example, coating material 8 may include polyurethane. Clip 9 is attached to wire body 7 at or within 15 centimeters of the distal end of wire body 7. Material of clip 9 may include a metallic material, a plastic material, a rubber material, a silicone material, or any combination of metallic, silicone, rubber, and/or plastic materials. For example, material of clip 9 may include polyurethane, silicone, or a combination thereof. As described further below, clip 9 is capable of holding color changing pH indicator 13.

FIG. 2 depicts a perspective view of an exemplary clip 9 in an open position with an exemplary color changing pH indicator 13, where the color changing pH indicator is not yet installed onto a bottom cover 11 of the clip 9. Clip 9 includes a top cover 10 and a bottom cover 11, the bottom cover 11 being movably connected to the top cover 10. Clip 9 is capable of being in an open position or a closed position. Top cover 10 forms a convex surface and two oblong side walls, together defining an inner chamber. As an example, shown in FIG. 2, the convex surface of top cover 10 is half-oval shaped, which may facilitate movement of clip 9 inside a lumen, such as inside nasogastric tube 1 in FIG. 1. Top cover 10 includes a latch 17 being capable of locking clip 9 in a closed position. Bottom cover 11 includes a plurality of protrusions 12 that project towards the inner chamber defined by top cover 10 when clip 9 is in a closed position. Plurality of protrusions 12 may be arranged in one or more rows (e.g., six protrusions in two rows with three protrusions per row). Color changing pH indicator 13 forms one or more holes 14 through color changing pH indicator 13. Also, color changing pH indicator 13 may form a central hole 16 through color changing pH indicator 13 and/or forms plurality of holes 14 (e.g., six holes in two rows with three holes per row) that correspond to plurality of protrusions 12 of bottom cover 11. Latch 17 of clip 9 is capable of inserting through central hole 16 of color changing pH indicator 13 when clip 9 is in a closed position.

FIG. 3 depicts a perspective view of an exemplary clip 9 in an open position with an exemplary color changing pH indicator 13. Color changing pH indicator 13 is installed onto bottom cover 11 of clip 9 through engagement of plurality of protrusions 12 of bottom cover 11 into the corresponding plurality of holes 14 of color changing pH indicator 13. Further, upon installation onto bottom cover 11, central hole 16 of color changing pH indicator 13 is aligned into a position where latch 17 of top cover 10 can insert through central hole 16 to lock clip 9 in a closed position.

FIG. 4 depicts a perspective view of an exemplary clip 9 in a closed position with an exemplary installed color changing pH indicator 13. Clip 9 is locked in a closed position by latch 17 of top cover 10, and latch 17 inserts through central hole 16 of color changing pH indicator 13 to lock clip 9 in the closed position. Top cover 10 and bottom cover 11 are secured by latch 17 in the closed position, with a portion of installed color changing pH indicator 13 extending outside clip 9.

FIG. 5 depicts a perspective view of an exemplary disassembled clip. Top cover 10 forms two side slots 18 at a proximal end of the top cover. Bottom cover 11 forms a ring holder 19 at a proximal end of the bottom cover 11. Top cover 10 and the bottom cover 11 are connected by a hinge. The hinge includes axial pin 20, and axial pin 20 contacts ring holder 19 and two side slots 18 to form a movable connection between top cover 10 and bottom cover 11. Material of axial pin 20 may include a metallic material, a plastic material, a silicone material, a rubber material, or any combination of metallic, silicone, rubber, and/or plastic materials. As an example, material of axial pin 20 may be plastic.

FIG. 6 depicts a perspective view of an exemplary partially assembled clip. In this view, ring holder 19 is positioned inside top cover 11 and is adjacent to side slots 18. Axial pin 20 is being inserted into ring holder 19 through two side slots 18 (from one side slot to the other side slot). After axial pin 20 is fully inserted into ring holder 19, bottom cover 11 may rotate around axial pin 20 in relation to top cover 10 between an open position and a closed position. When top cover 10 and bottom cover 11 are in an open position, color changing pH indicator 13 may be installed, removed, and/or replaced.

FIG. 7 depicts a cross-sectional view of insertion of an exemplary nasogastric tube 1 and an exemplary guide wire

5 into stomach 21 of a patient. A nasogastric tube assembly may include nasogastric tube 1 and guide wire 5. Nasogastric tube 1 may be any one of the nasogastric tubes disclosed herein (e.g., as in FIG. 1). Guide wire 5 may be any one of the guide wires disclosed herein, including any of the components thereof (e.g., wire bodies, clips, and color changing pH indicators as in FIGS. 1-6). Guide wire 5 may be preloaded inside nasogastric tube 1 before nasogastric tube 1 is inserted in a patient. Alternatively and/or additionally, guide wire 5 may be inserted, retracted, and/or reinserted inside nasogastric tube 1 after nasogastric tube 1 is already inserted in a patient.

The nasogastric tube assembly may be placed in stomach 21 by inserting the nasogastric tube assembly into the esophagus, stomach, and/or lungs via a mouth or a nose of a patient. After the nasogastric tube assembly is placed in stomach 21, gastric juice 22 flows inside nasogastric tube 1 through one or more pores at a distal end of nasogastric tube 1 (e.g., pores 4 as in FIG. 1) and thus contacts a color changing pH indicator carried by clip 9 (e.g., color changing pH indicator 13 as in FIGS. 1-4 and clip 9 as in FIGS. 1-6). Because gastric juice 22 is acidic and may have a pH level from 1.5 to 2.0, the color changing pH indicator carried by clip 9 will display a color change after contacting gastric juice 22. Guide wire 5 may be pulled out from nasogastric tube 1 to retrieve the color changing pH indicator 13 carried by clip 9 at a distal end of guide wire 5. A person or machine can thus view or read the displayed color change to ascertain if the color changing pH indicator 13 carried by clip 9 has been in contact with gastric juice 22 and thus determine if nasogastric tube 1 is correctly placed inside stomach 21. In case the color changing pH indicator 13 carried by clip 9 does not display a color change or does not display a color change expected if contacted by gastric juice 22, latch 17 can be unlocked to change clip 9 from a closed position to an open position. The used color changing pH indicator 13 can be removed at the open position, and a new color changing pH indicator or another indicator of a different type (e.g., temperature indicator, indicator for the presence of a small molecule or a large molecule, etc.) may be installed. Afterwards, the clip 9 can be returned from the open position to the closed position and lock latch 17 to secure the newly installed indicator. Guide wire 5 and clip 9 may be sterilized before, during, or after removal and/or replacement of the indicator. Thus, guide wire 5 with a newly installed indicator may be ready to be inserted inside nasogastric tube 1 for another test. The aforementioned process may be repeated one or more times, such as until the color changing pH indicator displays a color change indicating nasogastric tube 1 is correctly placed inside stomach 21.

Additionally, the placement of nasogastric tube 1 may be adjusted, including partially retracting the nasogastric tube 1 from the esophagus, stomach 21, and/or lungs. Guide wire 5 may be reinserted, with a newly installed color changing pH indicator or another indicator, into nasogastric tube 1 before, during, or after at least partially retracting nasogastric tube 1. Nasogastric tube 1 may then be reinserted into the esophagus, stomach, and/or lungs.

Embodiments of the present apparatuses may be implemented as a variety of types of tubes and guide wires. For example, in addition to nasogastric tubes, the present apparatuses may be implemented as other types of tubes or tubes with other types of functionalities (e.g., orogastric tubes).

Any of the apparatuses, systems, and any of the components disclosed herein may be comprised in a kit. For example, components disclosed in any of the drawings may be packaged into a ready-to-use kit (e.g., color changing pH indicator 13 may be preloaded onto clip 9, and guide wire 5 may be preloaded inside nasogastric tube 1).

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the devices are not intended to be limited to the particular forms disclosed. Rather, they include all modifications and alternatives falling within the scope of the claims, and embodiments other than the one shown may include some or all of the features of the depicted embodiment. For example, components may be omitted or combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A guide wire for use in a nasogastric tube, the guide wire comprising:

a wire body comprising a distal end and a proximal end;

a clip attached to the wire body at or within 15 centimeters of the distal end of the wire body, the clip comprising a top cover and a bottom cover, the bottom cover being movably connected to the top cover, the clip being capable of being in an open position or a closed position; and a color changing pH indicator, wherein in the closed position the clip is capable of holding the color changing pH indicator and wherein in the open position the clip is capable of releasing the color changing pH indicator.

2. The guide wire of claim 1, wherein the guide wire further comprising an enlarged head at the proximal end of the wire body.

3. The guide wire of claim 1, wherein material of the wire body comprises a base material and a coating material.

4. The guide wire of claim 3, wherein the base material comprises flexible steel and/or wherein the coating material comprises polyurethane.

5. The guide wire of claim 1, wherein material of the clip comprises polyurethane, silicone, or a combination thereof.

6. The guide wire of claim 1, wherein the top cover forms a convex surface and two oblong side walls, together defining an inner chamber.

7. The guide wire of claim 6, wherein the convex surface is half-oval shaped.

8. The guide wire of claim 1, wherein the top cover and the bottom cover are connected by a hinge.

9. The guide wire of claim 8, wherein the top cover forms two side slots at a proximal end of the top cover, the bottom cover forms a ring holder at a proximal end of the bottom cover, and the hinge comprises an axial pin, wherein the axial pin contacts the ring holder and the two side slots to form a movable connection between the top cover and the bottom cover.

10. The guide wire of claim 1, wherein the bottom cover comprises a plurality of protrusions that project towards an inner chamber defined by the top cover when the clip is in the closed position.

11. The guide wire of claim 10, wherein the plurality of protrusions are arranged in one or more rows.

12. The guide wire of claim 1, wherein the color changing pH indicator forms one or more holes through the color changing pH indicator.

13. The guide wire of claim 1, wherein the color changing pH indicator forms a central hole through the color changing pH indicator and/or forms a plurality of holes that correspond to a plurality of protrusions of the bottom cover.

14. The guide wire of claim 1, wherein the top cover comprises a latch being capable of locking the clip in the closed position.

15. The guide wire of claim 14, wherein the latch is capable of inserting through a central hole of the color changing pH indicator when the clip is in the closed position.

16. A nasogastric tube assembly comprising:

a nasogastric tube; and the guide wire of claim 1.

17. The nasogastric tube assembly of claim 16, wherein the nasogastric tube comprises a distal end and a proximal end and wherein the nasogastric tube comprises one or more pores at the distal end of the nasogastric tube.

18. A method of placing a nasogastric tube assembly in a stomach, the method comprising:

inserting the nasogastric tube assembly of claim 16 into the esophagus, stomach, and/or lungs via a mouth or a nose; and removing the guide wire from the nasogastric tube to view the color changing pH indicator.

19. The method of claim 18, further comprising replacing the color changing pH indicator with another color changing pH indicator.

20. The method of claim 18, further comprising at least partially retracting the nasogastric tube from the esophagus, stomach, and/or lungs, reinserting the guide wire into the nasogastric tube before, during, or after at least partially retracting the nasogastric tube, and reinserting the nasogastric tube into the esophagus, stomach, and/or lungs.

* * * * *